United States Patent
Ishino et al.

(10) Patent No.: US 7,863,467 B2
(45) Date of Patent: Jan. 4, 2011

(54) METHOD FOR PRODUCING PROPYLENE OXIDE

(75) Inventors: Masaru Ishino, Sodegaura (JP); Hiroaki Abekawa, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 46 days.

(21) Appl. No.: 10/593,267

(22) PCT Filed: Mar. 18, 2005

(86) PCT No.: PCT/JP2005/005597

§ 371 (c)(1),
(2), (4) Date: Sep. 18, 2006

(87) PCT Pub. No.: WO2005/090323

PCT Pub. Date: Sep. 29, 2005

(65) Prior Publication Data

US 2008/0026938 A1    Jan. 31, 2008

(30) Foreign Application Priority Data

Mar. 22, 2004  (JP) .............................. 2004-082144

(51) Int. Cl.
C07D 301/12  (2006.01)
(52) U.S. Cl. .................. 549/533; 549/531; 502/242
(58) Field of Classification Search .................. 549/531, 549/533; 502/242
See application file for complete search history.

(56) References Cited

U.S. PATENT DOCUMENTS

2004/0034258 A1    2/2004  Oguchi et al.
2005/0182264 A1*   8/2005  Abekawa et al. ............ 549/531

FOREIGN PATENT DOCUMENTS

| CA | 2 524 730 A1 | 11/2004 |
|---|---|---|
| EP | 1 489 075 A1 | 12/2004 |
| EP | 1 580 190 A1 | 9/2005 |
| WO | WO 03/074421 A1 | 9/2003 |
| WO | WO 03/074422 A1 | 9/2003 |

OTHER PUBLICATIONS

Fan, Weibin et al., "A Titanosilicate That Is Structurally Analogous to an MWW-Type Lamellar Precursor", Angew. Chem. Int. Ed., 2004, vol. 43, pp. 236-240.
Sugimoto, Kaori et al., "Synthesis of MWW type titanosilicate by fluoride method and catalytic characterization", 2003, pp. 77.
Wu, Peng et al., "Preparation of Ti-MWW and specificity as liquid phase oxidation catalyst", Skokubai, Catalysis & Catalysis, 2001, vol. 43, pp. 158-160.
Wu, Peng et al., "Preparation of B-free Ti-MWW through reversible structural conversion", Chem. Comm., 2002, pp. 1026-1027.
Wu, Peng et al., "Hydrothermal Synthesis of a Novel Titanosilicate with MWW Topology", Chemistry Letters, 2000. pp. 774-775.
Wu, Peng et al., "A Novel Titanosilicate with MWW Structure: ii. Catalytic Properties in the Selective Oxidation of Alkenes", J. Catalysis, 2001, vol. 202, pp. 245-255.
Wu et al., "Improvement of Activity of Ti-MWW Catalyst by Post Treatment"; Catalysts & Catalysis, Mar. 2003, vol. 45, No. 2, pp. 107-110, with Translation (13 pgs.).

* cited by examiner

Primary Examiner—Janet L Andres
Assistant Examiner—David E Gallis
(74) Attorney, Agent, or Firm—Foley & Lardner LLP

(57) ABSTRACT

The present invention relates to a method for producing propylene oxide, characterized in that peroxide is reacted with propylene in the presence of a titanosilicate catalyst which has an X-ray diffraction pattern of the values indicated below and is represented by the formula.

$$xTiO_2 \cdot (1-x)SiO_2$$

(In the formula, x denotes a numerical value of 0.0001 to 0.1.)
X-ray diffraction patterns
(interplanar spacing of lattice d/Å)
13.2±0.6
12.3±0.3
11.0±0.3
9.0±0.3
6.8±0.3
3.9±0.2
3.5±0.1
3.4±0.1.

4 Claims, 1 Drawing Sheet

METHOD FOR PRODUCING PROPYLENE OXIDE

TECHNICAL FIELD

The present invention relates to a method for producing propylene oxide.

BACKGROUND ART

A technique for reacting peroxide with propylene in the presence of a Ti (titanium)-MWW catalyst to produce propylene oxide is disclosed in Japanese Unexamined Patent Publication No. 2003-327581. However, the catalyst has had a problem in view of catalyst costs due to long and complicated processes to produce it.

DISCLOSURE OF THE INVENTION

Figure 1:
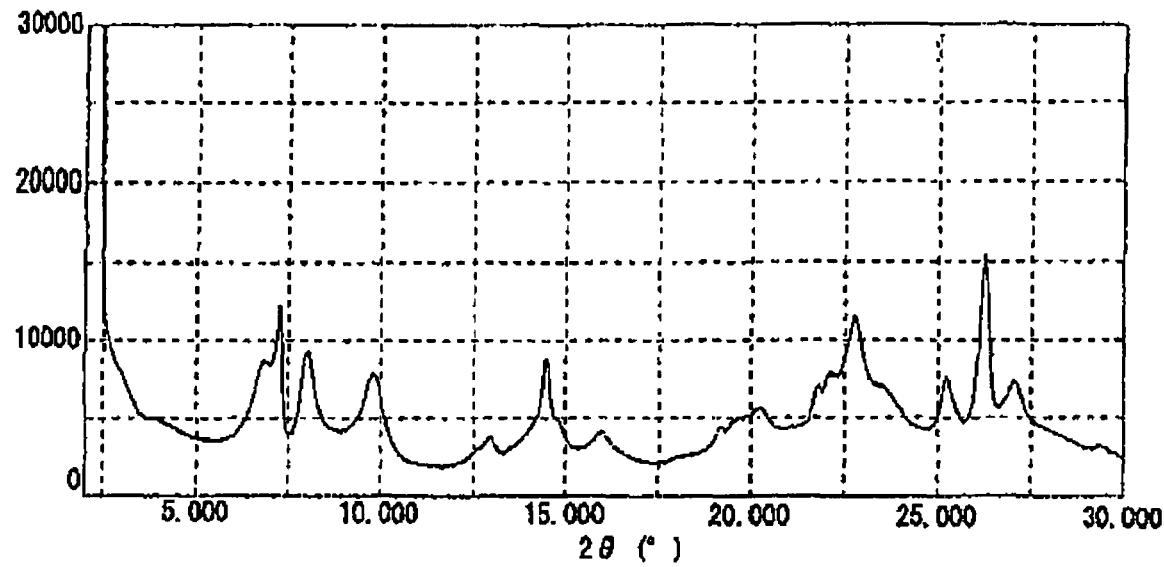
FIG. 1 is a chart showing an X-ray diffraction pattern of a Ti (titanium)-MWW precursor catalyst used in Example 1.
Figure 2:
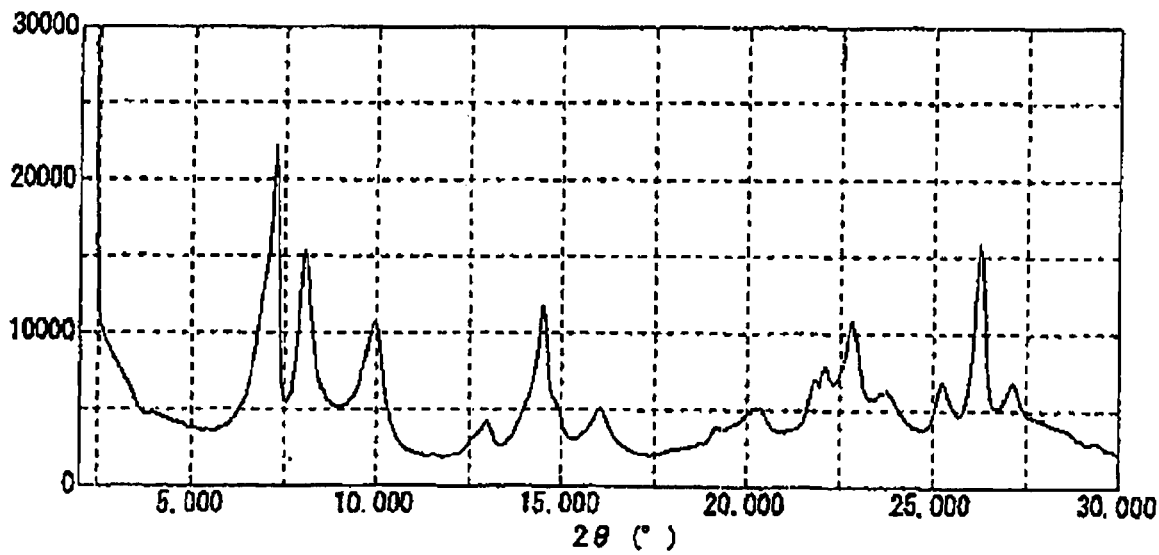
FIG. 2 is a chart showing an X-ray diffraction pattern of a Ti (titanium)-MWW catalyst used in Comparative Example 1.

The horizontal axis of FIGS. 1 and 2 denotes angle of diffraction 2θ (°), and the vertical axis denotes intensity (cps: count per second).

According to the present invention, propylene oxide can be produced by using a catalyst for producing propylene oxide, which catalyst is excellent in that it can be prepared at inexpensive costs without requiring more complicated processes.

That is, the present invention relates to a method for producing propylene oxide, characterized in that peroxide is reacted with propylene in the presence of a titanosilicate catalyst which has an X-ray diffraction pattern as indicated below and is represented by the formula.

$$xTiO_2 \cdot (1-x)SiO_2$$

wherein x denotes a numerical value of 0.0001 to 0.1.
Said X-ray diffraction patterns
(interplanar spacing of lattice d/Å)
13.2±0.6
12.3±0.3
11.0±0.3
9.0±0.3
6.8±0.3
3.9±0.2
3.5±0.1
3.4±0.1

BEST MODE FOR CARRYING OUT THE INVENTION

The above-mentioned X-ray diffraction patterns of a catalyst used in the present invention can be measured by using a conventional X-ray diffractometer employing copper K-α radiation.

A catalyst of the present invention has all of the above-mentioned X-ray diffraction patterns. In the present invention, typically, X-ray diffraction peak intensity denotes a local maximum value in the above-mentioned interplanar spacing of lattice, and may be found as a shoulder peak in the case where an X-ray diffraction peak of impurities or mixtures and an X-ray diffraction peak of the catalyst of the present invention overlap each other.

Among the above-mentioned X-ray diffraction patterns, a peak of d=13.2±0.6 Å is characteristic of the catalyst of the present invention. The peak of d=13.2±0.6 Å exists around 2θ (θ is Bragg angle)=6.7° in the case of using copper K-α radiation employed in a conventional X-ray diffractometer, and it is known that this peak is a peak derived from (002) lattice plane and specific to a layer structure of an MWW type layered precursor as described in 'Catalyst', 158, vol. 43, (2001).

The catalyst of the present invention is titanosilicate represented by the formula $xTiO_2 \cdot (1-x)SiO_2$ wherein x denotes a numerical value of 0.0001 to 0.1, and a method for producing the same, as a layered precursor of Ti-MWW zeolite, has been known in 'Chemistry Letters', 774-775, (2000), Japanese Unexamined Patent Publication No. 2003-32745 or 'Chemical Communication', 1026-1027, (2002). That is, the first method is generally called a hydrothermal synthesis method. The Ti-MWW precursor is obtained by heating a mixture containing a structure directing agent, a titanium-containing compound, a boron-containing compound, a silicon-containing compound and water. The Ti-MWW precursor is generally used as a catalyst after removing the structure directing agent in the fine pores.

The second method is generally called a reversible structural conversion method or a post-synthesis method. A mixture containing a structure directing agent, a boron-containing compound, a silicon-containing compound and water is heated to obtain a B (boron)-MWW precursor, which is calcined preferably after removing the structure directing agent in the fine pores to obtain B (boron)-MWW. The obtained B (boron)-MWW is deboronized by acid and then a mixture formed adding a structure directing agent, a titanium-containing compound and water is heated to produce a Ti-MWW precursor. The Ti-MWW precursor is generally used as a catalyst after removing the structure directing agent in fine pores and drying.

Examples of the structure directing agent include piperidine, hexamethyleneimine and the like. Examples of the titanium-containing compound include tetraalkyl orthotitanate such as tetra-n-butyl orthotitanate, titanium halide or the like. Examples of the boron-containing compound include boric acid and the like. Examples of the silicon-containing compound include tetraalkyl orthosilicate such as tetraethyl orthosilicate, fumed silica or the like.

A mixture containing the structure directing agent, the titanium-containing compound, the boron-containing compound, the silicon-containing compound and water is heated at typically 100 to 200° C. The heating temperature of the mixture is typically raised at a rate of 0.01 to 2° C./minute. The heating time is typically approximately 2 to 240 hours. A hydrothermal synthesis method to be performed under autogenous pressure of the mixture is generally known as a heating method. The hydrothermal synthesis method is mostly conducted in a batch method but may be conducted in a flow method.

As described in 'Soritu 45 Shunen Kinen Osaka Taikai Tokubetu Koen Shotai Koen Dai 33 Kai Sekiyu/Sekiyu Kagaku Toronkai Kouen youshi', 77, (2003), MWW zeolite as seed crystal or hydrofluoric acid can also be added to a mixture containing a structure directing agent, a titanium-containing compound, a boron-containing compound, a silicon-containing compound and water.

As a method of treating a Ti-MWW precursor with acids such as nitric acid, sulfuric acid or the like there is a known method by removing the structure directing agent in the fine pores. The Ti-MWW precursor is treated with an acid, thereafter separated from the acid by filtration, washed with water if necessary, dried and used as a catalyst.

The drying temperature is generally 20° C. or more and less than 200° C. Too higher drying temperature requires more energy costs for heating. Too lower drying temperature requires more costs because drying time is prolonged and resulted in lowered production efficiency.

The following methods are known as a drying method: a method of heating by a drier, a method of drying by sending heated gas and a method of drying by using a spray drier that can simultaneously dry and form particles of approximately 1 to 1000 μm. In case of using a spray drier, the inlet temperature of hot air occasionally exceeds 200° C., which is necessary heat for vaporizing a liquid and does not deteriorate the effect of the present invention as long as the outlet temperature of hot air is less than 200° C.

In case of using the catalyst in a slurry reactor or a fluidized-bed reactor, a method of drying by using a spray drier is preferable because it can simultaneous form and dry it.

The present catalyst preparation method of the invention is advantageous in that sufficient calcination for crystallizing is not necessary. In case of using Ti-MWW as a catalyst, the Ti-MWW precursor is dried and thereafter needs to be calcined sufficiently for crystallizing; however, calcination is not always necessary in the present invention, and sufficient calcination for crystallizing does not need to be performed even though calcination is performed. The sufficient calcination requires so excessive costs that it impairs the effect of the present invention. That is, the catalyst of the present invention can be produced at an inexpensive cost as compared with Ti-MWW by not being sufficiently calcinated.

As described in 'Zeoraito no Kagaku to Kogaku' (Kodansha Scientific Ltd., 10, (2000)), it is known that the interlayer is subject to dehydration condensation to form an MWW structure, namely, cause crystallization into an MWW structure by raising the temperature of drying than 200° C. and further retaining the higher temperature for a long time. This operation is called calcination and distinguished from drying. The occurrence of crystallization into an MWW structure by calcination can be confirmed by measuring an X-ray diffraction pattern, namely, obtaining an X-ray diffraction pattern as shown in FIG. 2 in the case of using copper K-α radiation. It can be confirmed that a peak in the proximity of 2θ=6.7° derived from a interplanar spacing of lattice of d=13.2±0.6 Å disappears in the obtained X-ray diffraction pattern. The reason therefor is that a spacing between Ti-MWW precursor layers is decreased by dehydration condensation, and the peak overlaps with a peak in the proximity of 2θ=7.2° derived from a interplanar spacing of lattice of d=12.3±0.3 Å.

This calcination is known as the most convenient method for crystallization from an MWW precursor into an MWW structure. That is, sufficient calcination of an MWW precursor allows the dehydration condensation of the interlayer of the MWW precursor, so that crystallization is promoted to form an MWW structure. It is described in Japanese Unexamined Patent Publication No. 2003-32745 that the calcination temperature is preferably 200 to 700° C., most preferably 400 to 600° C. The calcination time is generally approximately 1 to 100 hours. Lower calcination temperature allows energy per unit of time to be decreased; however, longer calcination time becomes so necessary as to decrease production efficiency and thereby require excessive costs. Higher calcination temperature causes necessary energy to increase so that excessive costs are required.

The catalyst of the present invention does not require crystallization from an MWW precursor into an MWW structure, so that sufficient calcination in producing the catalyst is unnecessary. In particular, the catalyst of the present invention is most suitably produced by the process of producing a catalyst without having calcination operations. That is, without employing the calcination operations the catalyst production cost is more inexpensive.

As it is described in 'Catalyst & Catalysis', 158, vol. 43, (2001), the catalyst of the present invention is known to have the peak intensity of an X-ray diffraction pattern to be obtained varies greatly with the catalyst preparation conditions, and a peak of sharp and strong intensity is occasionally found, while as shown in FIG. 1 of the present invention only a weak and broad peak as compared with an MWW structure is occasionally found. To our surprise, however, the catalyst of the present invention can maintain high catalytic activity even when only a weak and broad peak is found.

The catalyst of the present invention is a catalyst used for producing propylene oxide by performing an epoxidation reaction of propylene with the use of peroxide.

Examples of the peroxide include inorganic peroxide such as hydrogen peroxide or the like, and organic peroxide such as cumene hydroperoxide or the like. Among these, hydrogen peroxide is preferable for the ready availability of raw materials thereto.

A description is made to the method for producing propylene oxide comprising an epoxidation reaction of propylene with the use of peroxide in the presence of a catalyst of the present invention.

In the present invention, the reaction can also be conducted in the presence of a solvent. Examples of the solvent that may be used include water, an organic solvent, supercritical fluid and the like. Examples of the organic solvent include an alcohol such as tert-butanol or the like, a ketone compound such as acetone or the like, an ether compound such as methyl-tert-butyl ether or the like, an ester compound such as ethyl acetate or the like, a nitrile compound such as acetonitrile, propionitrile or the like, an aliphatic hydrocarbon such as n-heptane or the like, an aromatic hydrocarbons such as toluene, cumene or the like, a halogenated hydrocarbon such as 1,2-dichloroethane or the like, and various organic compounds. Examples of the supercritical fluid include carbon dioxide or the like. Preferred solvents include the alcohol solvent, and preferred alcohol solvents include tert-butanol.

The catalyst used for the present invention can show particularly higher activity as compared with Ti-MWW catalyst when a solvent having such a big molecule as comprising 4 or more elements except hydrogen atom(s) is used.

Examples of the method of supplying hydrogen peroxide used for the present invention include a method of supplying a hydrogen peroxide solution previously produced, or a method of supplying hydrogen peroxide synthesized in situ. Examples of the method of synthesizing hydrogen peroxide in situ include a method of synthesizing hydrogen peroxide by using a transition metal catalyst such as Pd, Au or the like for synthesizing hydrogen peroxide in situ from hydrogen and oxygen, which is supported on or mixed with the catalyst of the present invention.

Examples of the method of supplying cumene hydroperoxide used for the present invention include a method of supplying cumene hydroperoxide obtained by oxidizing cumene with oxygen.

An epoxidation reaction of propylene by the present invention is usually carried out at a reaction temperature typically from 0 to 150° C. and under a reaction pressure typically of from 0.1 to 20 MPa.

Examples of the reaction method include a fixed-bed flow reaction method and a slurry reaction method.

EXAMPLES

Next, the present invention is described by referring to examples.

Example 1

The present invention is described by way of examples. That is, gel comprising 9.1 kg of piperidine, 25.6 kg of pure water, 6.2 kg of boric acid, 0.54 kg of TBOT (tetra-n-butyl orthotitanate) and 4.5 kg of fumed silica (cab-o-sil M7D) was prepared in an autoclave at room temperature under an atmosphere of air while stirred, and aged for 1.5 hours and thereafter tightly closed. The gel was heated-up over 10 hours under stirring, and thereafter retained at a temperature of 170° C. for 168 hours to thereby obtain a suspension by hydrothermal synthesis. The obtained suspension was filtered and thereafter washed with water until the filtrate showed around pH 10. Next, the filter cake was dried at a temperature of 50° C. to obtain white powder, which still contained water. 3.5 L of 13 wt % nitric acid was added to 350 g of the obtained powder and refluxed for 20 hours. Subsequently, the powder was filtered, washed with water to the proximity of neutrality and sufficiently dried at a temperature of 50° C. to obtain 98 g of white powder. With regard to this white powder, an X-ray diffraction pattern was measured by using an X-ray diffractometer employing copper K-α radiation to obtain the X-ray diffraction pattern shown in FIG. 1. It was confirmed that the powder was a Ti (titanium)-MWW precursor, which was known by the change after calcinations of the obtained white powder into Ti-MWW as shown in FIG. 2.

| 2θ/° | interplanar spacing of lattice d/Å |
|---|---|
| 6.82 | 13.0 |
| 7.23 | 12.2 |
| 7.97 | 11.1 |
| 9.78 | 9.0 |
| 12.9 | 6.8 |
| 22.7 | 3.9 |
| 25.2 | 3.5 |
| 26.2 | 3.4 |

The reaction was performed by using this Ti (titanium)-MWW precursor catalyst.

That is, 36% —$H_2O_2$ aqueous solution, tert-butanol and pure water were mixed well to prepare a solution of $H_2O_2$: 5 wt %, water: 47.5 wt %, tert-butanol: 47.5 wt %. 12 g of the prepared solution and 0.010 g of the pulverized Ti (titanium)-MWW precursor catalyst were put into a 50-ml stainless-steel autoclave. Next, the autoclave was transferred onto an ice bath, which was filled with 10 g of liquefied propylene and further pressurized up to 2 MPa-G with nitrogen. The autoclave was put in a block bath made of aluminum so that the internal temperature became 40° C., and 5 minutes thereafter when the internal temperature rose up to approximately 35° C. was regarded as reaction initiation. 1 hour after the reaction initiation, the autoclave was taken out of a hot water bath to take a sample. The pressure in starting the sampling was 2.6 MPa-G. The analysis was conducted by using gas chromatography. As a result, propylene oxide production activity per unit catalyst weight was 0.781 mol·h$^{-1}$·g$^{-1}$.

Example 2

The reaction was conducted in a similar manner as in Example 1 by using the catalyst used in Example 1 except for using a solution, prepared by well mixing approximately 36 wt % aqueous $H_2O_2$ solution, acetonitrile and pure water to contain $H_2O_2$: 5 wt %, water: 47.5 wt %, acetonitrile: 47.5 wt %. As a result, propylene oxide production activity per unit catalyst weight was 0.319 mol·h$^{-1}$·g$^{-1}$.

Comparative Example 1

The Ti (titanium)-MWW precursor used in Example 1 was fired at a temperature of 530° C. for 6 hours to obtain Ti (titanium)-MWW catalyst powder. It was confirmed by measuring an X-ray diffraction pattern by using an X-ray diffractometer in a similar manner as in Example 1 that the obtained powder had an MWW structure (FIG. 2).

| 2θ/° | interplanar spacing of lattice d/Å |
|---|---|
| 7.24 | 12.2 |
| 8.02 | 11.0 |
| 9.94 | 8.9 |
| 12.9 | 6.8 |
| 22.8 | 3.9 |
| 25.2 | 3.5 |
| 26.2 | 3.4 |

The catalyst evaluation test was conducted in a similar procedure as in Example 1 by using 0.010 g of the obtained Ti (titanium)-MWW catalyst and a solution prepared to composed of $H_2O_2$: 5 wt %, water: 47.5 wt %, tert-butanol: 47.5 wt %. As a result, propylene oxide production activity per unit catalyst weight was 0.309 mol·h$^{-1}$·g$^{-1}$.

Comparative Example 2

The catalyst evaluation test was performed in the same manner as Example 2 except for using the Ti (titanium)-MWW catalyst used in Comparative Example 1. As a result, propylene oxide production activity per unit catalyst weight was 0.300 mol·h$^{-1}$·g$^{-1}$.

INDUSTRIAL APPLICABILITY

The present invention can provide a catalyst for producing propylene oxide, which is used for producing propylene oxide by carrying out an epoxidation reaction of propylene with an oxide, and has advantageous in that it can be prepared at inexpensive costs without requiring more complicated processes while it has an activity equal to or higher than that of conventionally known catalysts, and a method for producing propylene oxide by using the catalyst.

What is claimed is:

1. A method for producing propylene oxide, characterized in that hydrogen peroxide is reacted with propylene in the presence of a titanosilicate catalyst which has an X-ray diffraction pattern indicated below and is represented by the formula:

$$xTiO_2 \cdot (1-x)SiO_2$$

wherein x denotes a numerical value of 0.0001 to 0.1;
X-ray diffraction patterns
(interplanar spacing of lattice d/Å)
13.2±0.6
12.3±0.3
11.0±0.3
9.0±0.3
6.8±0.3

3.9±0.2
3.5±0.1
3.4±0.1
and wherein the titanosilicate is a Ti-MWW precursor.

2. A method for producing propylene oxide according to claim 1, wherein the titanosilicate is titanosilicate synthesized by a hydrothermal synthesis method.

3. A method for producing propylene oxide according to claim 1, wherein alcohol is used as a solvent.

4. A method for producing propylene oxide according to claim 1, wherein tert-butanol is used as a solvent.

* * * * *